United States Patent
Denes et al.

(10) Patent No.: US 6,402,899 B1
(45) Date of Patent: Jun. 11, 2002

(54) PROCESS FOR INTERCALATION OF SPACER MOLECULES BETWEEN SUBSTRATES AND ACTIVE BIOMOLECULES

(75) Inventors: Ferencz S. Denes; Sorin O. Manolache; Majid Sarmadi; Raymond A. Young; Ramaswami Ganapathy; Alvaro de Jesus Martinez-Gomez, all of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/492,981

(22) Filed: Jan. 27, 2000

(51) Int. Cl.[7] .............................................. B01J 19/08

(52) U.S. Cl. ..................................................... 204/164

(58) Field of Search ........................................ 204/164

(56) References Cited

U.S. PATENT DOCUMENTS

| | | |
|---|---|---|
| 3,870,610 A | 3/1975 | Baird et al. |
| 4,676,195 A | 6/1987 | Yasui et al. |
| 5,000,831 A | 3/1991 | Osawa et al. |
| 5,034,265 A | 7/1991 | Hoffman et al. |
| 6,096,564 A | 8/2000 | Denes et al. |
| 6,159,531 A * | 12/2000 | Dang et al. ............... 427/2.24 |

OTHER PUBLICATIONS

Buddy D. Ratner, "Surface Modification of Polymers: Chemical, Biological and Surface Analytical Challenges," Biosensors & Bioelectronics, vol. 10, 1995, pp. 797–804. No Month Available.

F. Denes, et al., "Synthesis and Surface Functionalization Under Cold–Plasma Conditions," Journal of Photopolymer Science and Technology, vol. 12, No. 1, 1999, pp. 27–38. No Month Available.

F. Denes, et al., "Immobilization of Biomolecules on RF–Plasma Functionalized Polymer Surfaces," MACRO/98 Australia, Jul., 1998.

R. Ganapathy, et al., "Immobilization of α–Chymotrypsin on Oxygen–RF–Plasma Functionalized PET and PP Surfaces," J. Biomater. Sci. Polymer Edn., vol. 9, No. 4., 1998, pp. 389–404. No Month Available.

A.J. Martinez–Gonez, et al., "Plasma Enhanced Functionalization of Cellophane Surfaces (I) Implantation of Primary Amine Functionalities," 54th Southwest Regional Meeting of the American Chemical Society, Baton Rouge, Nov., 1998.

F. Denes, et al., "Mechanism of RF Plasma Induced Fragmentation of $SiCl_4$ and Surface Functionalization of Polymeric Substrates from $SiCl_x$ Species," J. Applied Polymer Science, vol. 61, 1996, pp. 875–884. No Month Available.

Z.Q. Hua, et al., "Surface Functionalization of Polymeric Substrates from Radio Frequency–Plasma–Generated Silylium Ions," J. Vac. Sci. Technol. A, vol. 14, No. 3, May/Jun. 1996, pp. 1339–1347.

* cited by examiner

Primary Examiner—Kishor Mayekar
(74) Attorney, Agent, or Firm—Foley & Lardner

(57) ABSTRACT

A wide variety of substrates can be functionalized to attach spacer molecules therein by exposing the substrates to a cold plasma ignited in dichlorosilane, silicon tetrachloride or hexachlorodisilane gas to implant silicon-chlorine functionalities in the substrate surface. The plasma implanted surface functionalities can then be utilized to initiate second stage gas phase derivatization reactions to form linker molecules attached to the substrate. Active biomolecules such as enzymes can then be bound to the exposed linker molecules to bind the bioactive molecules to the substrate while allowing freedom of movement and conformation of the bound molecule comparable to that of the free molecule.

36 Claims, 10 Drawing Sheets

PROCESS FOR INTERCALATION OF SPACER MOLECULES BETWEEN SUBSTRATES AND ACTIVE BIOMOLECULES

This invention was made with United States government support awarded by the following agency: NSF Grant No: 8721545. The United States has certain rights in this invention.

FIELD OF THE INVENTION

This invention pertains generally to the field of plasma processing of materials and to the functionalization of organic and inorganic polymeric substrates.

BACKGROUND OF THE INVENTION

Molecular recognition and molecular manufacturing systems developed from immobilized biomolecules (enzymes, oligonucleotides, cells) will play an essential role in advanced future technologies and medicine. The anchorage of bioactive molecules on specific substrate surfaces is the key element in the development of molecular assemblers. The inertness of the substrates, the nature of linkages between the substrates and biomolecules, the topographies of the host-surfaces, and the "chained-freedom" of the active molecules are characteristics which can be achieved only with difficulty using conventional chemistry approaches.

Molecular recognition between biological macromolecules, small molecules, macromolecules and specific surfaces plays a crucial role in the understanding of various biological systems and in the design of artificial, intelligent surfaces (molecular manufacturing systems) with tremendous practical potentials. As soon as a primitive molecular assembler which is able to self-replicate by atomic-precision-positional-control is constructed, migration pathways will allow the generation of increasingly sophisticated assemblers.

To understand the molecular basis of the interaction, controlled immobilization of biomolecules must be performed by taking into account the chemical and physical (crystallinity, morphology) structure of the substrates, the nature of the bonding between the biologically active molecules and substrates, the surface density of immobilized molecules, and the distance between the anchored biomolecules and the substrate. By understanding and controlling surface functionalization and the consequent anchoring reaction mechanisms, tailored and very specific reaction pathways can be developed (molecular recognition).

Polymer-bound oligonucleotides will find their applications in hybridization-based diagnostics and in the discovery of new therapeutics based on molecular recognition. Prenatal diagnostics of genetic aberrations, identification of virus born diseases, detection of mutations of regulatory proteins controlling carcinogenesis, and novel hybridization-based identification techniques oriented to forensic or archaeology fields are some of the potential applications.

Molecular recognition will also play an essential role in areas other than medicine, pharmaceutics and biotechnology. Development of ultra-selective chemical sensors and absorbent surfaces are crucial for creating environmentally safe processes. Monitoring the quality of water is one of the major demands in this area. Biomolecular-based chemical sensors and filters for toxic chemicals and microorganisms (e.g. *E. coli*) will play a significant role in future technologies.

Most of the natural and synthetic polymeric substrates can easily be functionalized through polymer-analog reactions. Main chain and side-group homogeneous reactions are the most common approaches. The use of polymers as "carriers" or "supports" for chemical reagents, catalysts or substrates represents a relatively new, significant, and rapidly developing area. The polymer is in the form of an insoluble, inert substrate that may be a solvent-swollen, crosslinked gel, or a surface active solid. This approach eases the separation of reagents or catalysts (e.g. enzymes) from the reaction products, permitting consequently the automation of the complex chemistry. However, the specific structure of the repeating units of the macromolecules often limit considerably the variety of polymer-analog reactions. These reactions are even more difficult to develop under heterogeneous environments. Natural and even some synthetic polymeric substrates can also undergo undesired chemical modifications, and sometimes biodegradation, during the polymer-supported organic reactions. Inert polymeric substrates (e.g. polyethylene, polypropylene, PET, PTFE) and inorganic supports (e.g. glass, silica) however, cannot be functionalized efficiently by using conventional wet chemistry approaches.

Cold plasma processing has shown promise for the functionalization of organic and inorganic substrates. See, e.g., D. T. Clark, et al., Polymer Surfaces (book), John Wiley & Sons, New York, 1978, pp. 185–210; F. Denes, et al., "Surface Modification of Polysaccharides Under Cold Plasma Conditions," in Polysaccharides. Structural Diversity and Functional Versatility (book), Ed. S. Dumitriu, Marcel Dekker, Inc., New York, 1998; Plasma Surface Modification of Polymers: Relevance to Adhesion (book), Eds. M. Strobel, et al., VSP, Utrecht, The Netherlands, 1994; F. Denes, TRIP, Vol., No. 1, 1997, pp. 23, et seq. Numerous experiments performed in recent years in plasma laboratories under various internal and external plasma conditions and reactor geometries clearly indicate that inert and reactive-gas discharges are effective for the surface modification (functionalization) of even the most inert materials, such as polypropylene, Teflon®, silica, etc. The industrial applications of macromolecular plasma chemistry are rapidly developing. Large capacity reactors and continuous flow system plasma installations have been designed, developed and tested.

The most widely used synthetic polymer surfaces are usually characterized by low surface energy values, and some of the thermoplastics, including polyethylene and polypropylene, for example, are essentially chemically inert. Modification of characteristics like adhesion, wettability, dyeability, and reactivity for such materials necessitates the creation of particular functionalities on the surfaces of such polymer substrates.

The advantages of using enzymes in chemical synthesis are related to their very high specificity (regio- and stereo-specificity) and versatility, mild reaction conditions (close to room temperatures and to pH neutral media), and to their high reaction rates. However, due to the poor recovery yields and reusability of free enzymes, much attention has been paid in the last few years to the development of efficient enzyme immobilization processes. Most biologically-active in vivo species, such as enzymes and antibodies, function in heterogeneous media. These environments are difficult to reproduce in vitro for industrial utilization. Immobilized enzyme systems are useful for experimental and theoretical research purposes for understanding the mechanisms of in vivo, bio-catalysed reactions, and offer solutions for use in batch-type reactions, where there is poor adaptability to various technological designs and recovery of the enzymes is difficult.

The molecular recognition ability and activity of enzymes (polypeptide molecules) are based on their complex three-dimensional structures containing sterically exposed, specific functionalities. The polypeptide chains are folded into one or several discrete units (domains), which represent the basic functional and three-dimensional structural entities. The cores of domains are composed of a combination of motifs which are combinations of secondary structure elements with a specific geometric arrangement. The molecular-structure-driven chain-folding mechanisms generate three-dimensional enzyme structures with protein molecules orienting their hydrophobic side chains toward the interior and exposing a hydrophilic surface. The —C(R)—CO—NH— based main chain is also organized into a secondary structure to neutralize its polar components through hydrogen bonds. These structural characteristics are extremely important and they make the enzyme molecules very sensitive to the morphological and functional characteristics of the potential immobilizing substrates. High surface-concentrations of enzyme-anchoring functionalities can result, for instance, in excessive enzyme-desities or multi-point connections which can "neutralize" the active sites or can alter the three-dimensional morphologies of the enzyme molecules through their mutual interaction and their interaction with the substrate surfaces. These are just a few of the factors which may be responsible for the significantly lower activities of immobilized-enzymes in comparison to the activities of free enzyme molecules. Rough substrate surface topographies or stereoregular surfaces (e.g., isotactic or syndiotactic polymers) might also influence, in a positive or negative way, the specific activities. Morphologically ordered surfaces might induce changes of the stereoregular shapes of protein molecules. It has also been found that enzymes can adopt more than one functional conformation other than its lowest potential energy state. E. S. Young, et al., Anal. Chem. Vol. 69, 1977, pp. 4242, et seq.

SUMMARY OF THE INVENTION

In accordance with the invention, silicon-chlorine atoms-based functionalities are implanted in substrates by exposing the substrates to a cold plasma of a gas selected from dichlorosilane, silicon tetrachloride, hexachlorodisilane and mixtures thereof. Various inorganic substrates such as glass and silica and organic substrates (e.g., polymers such as polyethylene, polycarbonate, polystyrene, etc.) may be efficiently functionalized in this manner. The substrates having plasma implanted surface functionalities can then be used to initiate gas phase in situ derivatization reactions to form linker molecules attached to the substrate. The reaction is carried out within the same reactor to avoid exposure of the functionalized surface to unwanted materials. After the plasma is terminated, the reactor reaction chamber is evacuated to remove the plasma forming gas and a selected reactant gas is introduced into the chamber and exposed to the substrate. Various suitable reactant gases may be utilized, examples of which include di-acylchloride derivatives, diamines and anhydrides, such as: ethlylenediamine, propylenediamine, hexafluoro 1,3 propylenediamine, pentafluoropropionic anhydride, hexafluoroglutaric anhydride, etc. The gas phase reaction may be carried out in multiple steps to provide a linked chain of spacer molecules of a desired length and structure. These spacer molecules are available for binding to various other reactants, particularly biomolecules including enzymes and nucleotides. For example, an enzyme that becomes bound to the substrate by the strands of spacer molecules can retain freedom of movement and conformation that is comparable to that of the free enzyme. In this manner, the activity of bioactive molecules such as enzymes and nucleotides can be significantly enhanced over that of such molecules bound directly to the substrate.

Further objects, features and advantages of the invention will be apparent from the following detailed description when taken in conjunction with the accompanying drawings.

DETAILED DESCRIPTION OF THE INVENTION

Figure 1:
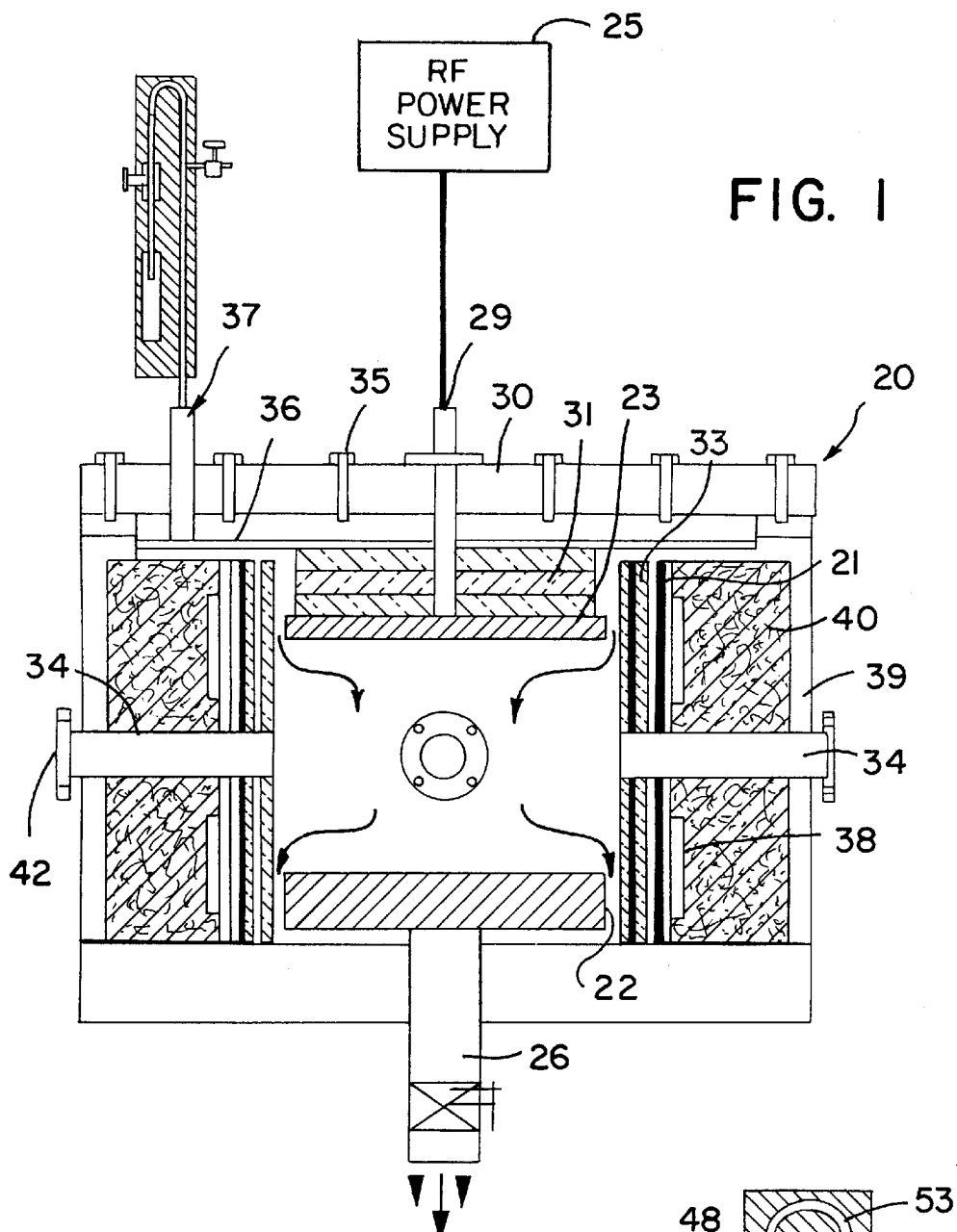
FIG. 1 is a cross-sectional view of a parallel plate plasma reactor with heating capabilities that may be utilized when carrying out the invention.

The intercalation of spacer molecules in accordance with the present invention is carried out utilizing cold-plasma processing techniques for initial functionalization of a substrate. Cold plasmas are non-thermal and non-equilibrium plasmas, as compared with hot plasmas which are thermal or equilibrium plasmas. In a cold plasma, the kinetic energy of the electrons is high while the kinetic energy of the atomic and molecular species are low; in a hot plasma, the kinetic energies of all species are high and organic materials would be damaged or destroyed in such plasmas.

In the present invention, the substrate to be treated is enclosed in a reaction chamber of the plasma reactor, a base pressure is established in the reactor, and a chloro-silicon gas, selected from the group consisting of dichlorosilane, silicontetrachloride, and hexachlorodisilane, and mixtures thereof, is introduced into the reaction chamber and a cold plasma is ignited in the gas. The surface of the substrate is exposed to the cold plasma for a selected period of time sufficient to react the plasma with the substrate to implant silicon-chlorine functionalities into the substrate surface. $SiCl_x$, $i_2Cl_x$ and $SiCl_xH_y$ plasma-generated charged and neutral (free radical) species are very reactive and can be attached covalently under in situ plasma environments to both inorganic and organic polymeric surfaces. Because of a large size of the silicon atom, the presence of D orbitals, and the trigonal planar or linear structures, these covalently linked functionalities are extremely reactive and can interact with many other functionalities, e.g., primary amine, carboxylic, etc. The plasma enhanced implantation of the silicon-chlorine functionalities onto substrate surfaces is preferably carried out under conditions which avoid extensive chlorine atom generation or the deposition of polyhalosilane-type structures. High chlorine atom concentrations can result in the development of intense surface chlorination reactions and in the formation and/or deposition of linear and cyclic polyhalosilane derivatives, which will largely not be attached covalently to the substrate surface. Such derivatives would, when exposed to moisture, generate silicon dioxide and polysilicic-acid type structures on the substrate surfaces, which would be barrier layers inhibiting the development of further derivatization reactions. The selection of the proper plasma parameters for the implantation of the silicon-chlorine based functionalities depend on the specific design of the reactor and on the relative geometric position of the target or substrate-holding electrode in the reaction chamber.

After the surfaces are functionalized, the reaction chamber is evacuated to remove the silicon-chlorine source gas, and a selected reactant gas is introduced into the chamber to covalently bond to the surface functionalities and form spacer molecules linked to the surface. The process can be repeated by evacuating the chamber to remove the first reactant gas and then introducing a second reactant gas which can bond to the first. In this manner, chains of linker molecules of a desired length can be built up, all of which are attached to the substrate surface. The last linker molecule in the chain may then be exposed to a biomolecule to which it will bond (for example, an enzyme) thereby providing active biomolecules bound to the substrate surface.

The present invention thus carries out the formation of the linker molecules in an in situ manner, with the spacer chains built up under vacuum conditions without removing the substrates from the plasma reactor. The process is a step-by-step gas phase reaction. After each step, the nonreacted components are evacuated from the reaction chamber. The nature and the length of the spacer chains can be controlled by the number of steps and by selecting the specific chain components. The process of the present invention has the particular advantage that it does not require any chemicals in addition to the spacer building-block molecules, in contrast to wet chemistry technologies which require complex mixtures of chemicals for the development of spacer chains.

For exemplification, the present invention is described utilizing plasmas formed in dichlorosilane gas as the silicon-chlorine source. However, the present invention may also be carried out utilizing silicon tetrachloride and hexachlorodisilane, and mixtures thereof, as the silicon-chlorine gas. The plasma induced functionalization of substrates utilizing such plasmas is described in F. Denes, et al., "Mechanism of RF Plasma Induced Fragmentation of $SiCl_x$ and Surface Functionalization of Polymeric Substrates from $SiCl_x$ Species," Journal of Applied Polymer Science, John Wiley & Sons, Inc., Vol. 61, 1996, pp. 875–84; and Z. Q. Hua, et al., "Surface Functionalization of Polymeric Substrates from Radio Frequency-Plasma-Generated Silylium Ions," J. Vac. Sci. Technol. A, Vol. 14, No. 3, May/June 1996, pp. 1339–47, which are incorporated herein by reference.

For exemplification of the invention, RF excitation, e.g., 40 kHz and pulsed and CW-13.56 MHz, of dichlorosilane in a cold-plasma, results in plasma-induced implantation of silicon-chlorine-hydrogen atoms-based ($SiCl_xHy$ where x and $y \leq 2$) functionalities onto inorganic substrates (e.g., glass, silica) and organic polymeric (polyethylene, cellophane, polycarbonate, etc.) substrates (e.g., sheets, beads, etc.).

The plasma implanted —$SiCl_xH_y$ surface functionalities can then be utilized to initiate second stage, in situ, gas phase derivatization reactions to form linker molecules attached to the substrate. Suitable gas phase reactants include e.g., (per-fluorinated compounds) di-acylchloride derivatives, diamines and anhydrides, such as: ethlylenediamine, propylenediamine, hexafluoro 1,3 propylenediamine, pentafluoropropionic anhydride, hexafluoroglutaric anhydride, etc. In this manner, step derivatization processes can be carried out to provide controlled structure and length of the spacer molecules.

In addition, longer spacer molecules intercalated between the polymeric substrate and the bioactive-molecule (e.g., an enzyme) can enhance significantly the activity of the immobilized enzymes. Enzyme activities that are comparable to that of the free enzyme can be achieved by the plasma-mediated spacer-molecule-intercalating process of the invention.

An example of a preferred parallel plate reactor provided with temperature control capabilities that can be utilized for plasma treatment in accordance with the invention is shown at 20 in FIG. 1. The reactor 20 is provided with heating capabilities (in the range of 25–500° C.) for the reaction chamber, the supply (dichlorosilane) reservoir, and the connecting stainless steel supply line. The reactor is composed of a cylindrical stainless steel reaction chamber 21 in which a 20 cm diameter and a 0.8 cm thick lower, grounded electrode 22 and an (identical dimensions) upper, stainless steel electrode 23 are located. The upper electrode 23 is connected to a conventional RF-power supply 25. Conventional power supplies are available at 40 kHz and 13.56 MHz (operable CW or pulsed). Typically, the MHz and kHz power supplies are separate units. Both electrodes are preferably removable, which facilitates post-plasma cleaning operations. The lower electrode 22 is also a part of the vacuum line 26 through supporting conically shaped and circularly-perforated stainless steel tubing. The evacuation of the chamber 21 is performed uniformly through the narrow gap (3 mm) existing between the lower electrode 22 and the bottom of the reaction chamber. The upper electrode 23 is directly connected to the threaded end of the vacuum-tight metal/ceramic feedthrough 29 which assures both the insulation of the RF-power line from the reactor and the dissipation of the RF-power to the electrodes. The space between the upper electrode and the upper wall 30 of the reaction chamber is occupied by three 1 cm thick and 20 cm diameter Pyrex-glass removable disks 31. These discs insulate the electrode from the stainless steel top of the reactor and allow adjustment of the electrode to electrode gap. The reactor volume located outside of the perimeter of the electrodes is occupied by two Pyrex-glass cylinders 33 provided with four symmetrically located through-holes 34 for diagnostic purposes. This reactor configuration substantially eliminates the non-plasma zones of the gas environment and reduces considerably the radial diffusion of the plasma species, leading consequently to a more uniform plasma-exposure of the substrates being treated. As a result, uniform surface treatments can be achieved. The removable top of the reactor allows the reaction chamber to be vacuum sealed with the aid of a copper gasket and fastening bolts 35. This part of the reactor also accommodates a narrow circular gas-mixing chamber 36 provided with a shower-type, 0.5 mm diameter orifices system, and with a gas supply connection 37. This gas supply configuration assures a uniform penetration and flow of the gases and vapors through the reaction zone. The entire reactor chamber can be heated with electric heaters 38 attached to the outside surface of the chamber. The reactor chamber is enclosed in an aluminum-sheet 39 which protects a glass-wool blanket 40 that surrounds the sides of the reactor chamber to reduce thermal energy loss. Four symmetrically positioned stainless steel porthole tubes pass through the insulating blanket and are connected and welded to the reactor wall for diagnostic purposes. These portholes are provided with exchangeable, optically smooth, quartz windows 42.

Figure 2:
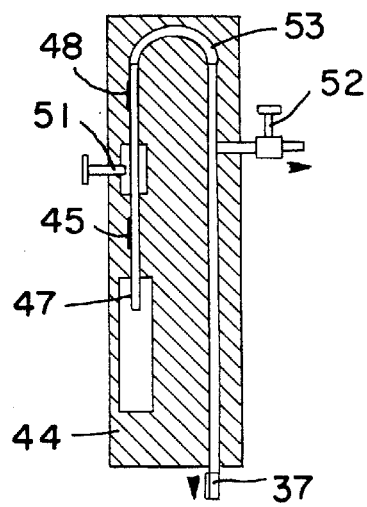
FIG. 2 is a more detailed cross-sectional view of a portion of the reactor of FIG. 1.
Figure 3:
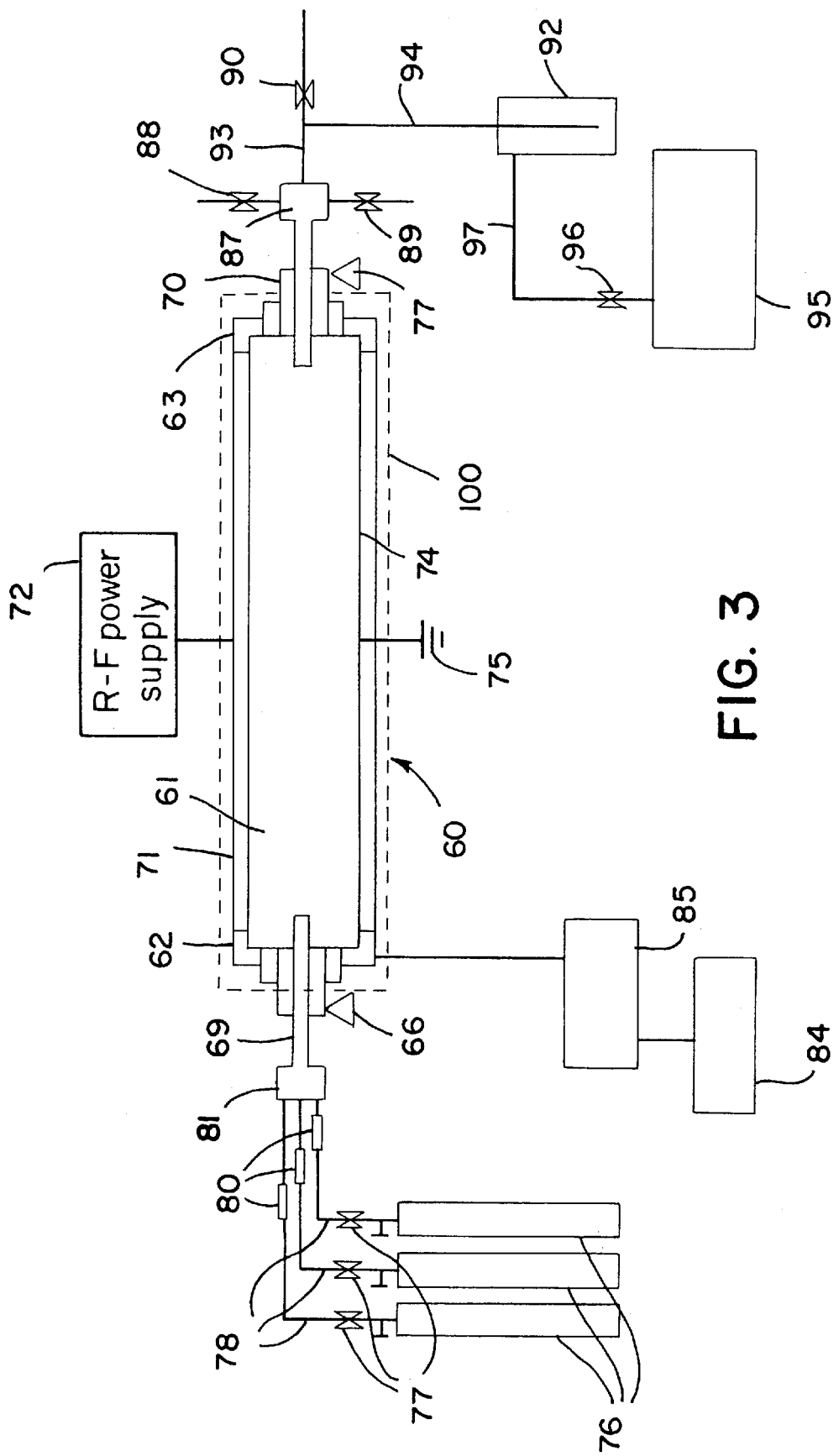
FIG. 3 is a simplified cross-sectional view of a rotary plasma reactor system that may be utilized in the present invention.

The gas reservoir, valve and the connecting stainless steel tubing are shown in greater detail in FIG. 2 and, as shown, are embedded in two shape-designed, 1 cm thick copper jackets 44 provided with controlled electric heaters 45, for processing low-volatility chemicals. The vapor supply assemblage is composed of a reservoir 47, VCR connectors 48, needle valves 51 and 52, and connecting tubing 53. The entire system is insulated using a glass-wool blanket coating.

The reactor 20 thus may be utilized to control the temperature of the reactor chamber and the substrate to achieve desired plasma operating conditions. Inductively coupled plasma reactors and other closed reactors may be utilized as well as corona discharge devices, examples of which are discussed below.

An exemplary cold plasma rotary reactor system which may be utilized to carry out the invention is shown generally at 60. Such a rotary system is especially well suited to the plasma treatment of fibers, powders and other particulate matter. The reactor system includes a cylindrical reaction vessel 61 (e.g., formed of Pyrex® glass, 1 m long and 10 cm inside diameter) which is closed at its two ends by disk shaped stainless steel sealing assemblies 62 and 63. The end assemblies 62 and 63 are mounted to mechanical support bearings 66 and 67 which engage the sealing assemblies 62 and 63 to enable rotation of the reaction vessel 61 about its central axis, i.e., the central axis of the cylindrical reaction vessel. Hollow shaft (e.g., 0.5" inside diameter) ferrofluidic feedthroughs 69 and 70 extend through the sealing assemblies 62 and 63, respectively, to enable introduction of gas into and exit of gas from the reaction chamber. A semicylindrical, outside located, copper upper electrode 71 is connected to an RF power supply 72, and a lower, similar semicylindrical copper electrode 74 is connected to ground (illustrated at 75). The two electrodes 71 and 74 closely conform to the cylindrical exterior of the reaction vessel 61 and are spaced slightly therefrom, and together extend over most of the outer periphery of the reaction vessel but are spaced from each other at their edges a sufficient distance to prevent arcing or discharge between the two electrodes.

The source gas is held in containers 76, e.g., storage tanks. The flow of gas from a source cylinder 76 is controlled by needle valves and pressure regulators 77 which may be manually or automatically operated. The gas that passes through the control valves 77 is conveyed along supply lines 78 through flow rate controllers 80 to a gas mixing chamber 81 (e.g., preferably of stainless steel), and an MKS pressure gauge (e.g., Baratron) may be connected to the mixing chamber 81 to monitor the pressure thereof. The mixing chamber 81 is connected to the feedthrough 69 that leads into the interior of the reaction chamber 61. A digital controller 84 controls a driver motor 85 that is connected to the assembly 62 to provide controlled driving of the reaction chamber in rotation.

The second feedthrough 70 is connected to an exhaust chamber 87 to which are connected selectively openable exhaust valves 88, 89 and 90, which may be connected to conduits for exhaust to the atmosphere or to appropriate recovery systems or other disposal routes of the exhaust gases. A liquid nitrogen trap 92 is connected to an exhaust line 93 which extends from the chamber 87 by stainless steel tubing 94. The trap 92 may be formed, e.g., of stainless steel (25 mm inside diameter). A mechanical pump 95 is connected through a large cross-section valve 96 via a tube 97 to the trap 92 to selectively provide vacuum draw on the reactor system to evacuate the interior of the reaction chamber 61 to a selected level.

The power supply 72 is preferably an RF power supply (e.g., 13.56 MHz, 1,000 W) which, when activated, provides RF power between the electrodes 71 and 74 to capacitively couple RF power to the gas in the reaction chamber within the reaction vessel 61. Conventional coils for inductively coupling RF power to the plasma may also be used (e.g., a coil extending around the reaction vessel 61). A Farraday cage 100 is preferably mounted around the exterior of the reaction vessel to provide RF shielding and to prevent accidental physical contact with the electrodes.

The reactor vessel may be rotated by the drive motor 85 at various selected rotational speeds (e.g., 30–200 rpm), and it is preferred that the vacuum pump and associated connections allow the pressure in the reaction chamber within the vessel to be selectively reduced down to 30 mT.

The following are examples of commercial parts that may be incorporated in the system 60: RF-power supply 85 (Plasma Therm Inc. RTE 73, Kresson N.J. 08053; AMNS-3000 E; AMNPS-1); mechanical vacuum pump 95 (Leibold-Heraeus/Vacuum Prod. Inc., Model: D30AC, Spectra Vac Inc); pressure gauge (MKS Baratron, Model: 622A01TAE); digitally controlled rotating system 84, 85 (DC motor Model 4Z528, Dayton Electric Mfg. Co.; DART Controls Inc. controller).

In utilization of the plasma treatment system 60 in accordance with the invention, it is generally preferred to carry out a plasma-enhanced cleaning of the reactor prior to treatment to eliminate possible contaminants. An exemplary cleaning step includes introduction of oxygen gas from one of the tanks 76 into the reaction chamber and ignition of a plasma in the gas at, e.g., a power level of 300 W, a gas pressure of 250 mT, an oxygen flow rate of 6 sccm, and a typical cleaning period of 15 minutes.

In a typical treatment, vacuum-dried fibers or particles are introduced into the reactor, the system is closed and the base pressure is created. The rotation of the reactor is started at the selected speed and the system is kept under these conditions for 30 minutes in order to complete the gas- and moisture-desorption from the extremely large substrate surfaces. In the next step the selected dichlorosilane gas flow and pressure conditions are established, and the plasma is ignited and sustained for the desired treatment time. At the end of the reaction, the system is evacuated to base pressure level, re-pressurized with argon, and the sample is removed and stored in vacuum desiccator until analytical procedures and/or second stage reactions (composite preparations) are initiated.

Plasma treatments are preferably preceded by a decontamination procedure of the reactor by igniting oxygen and argon plasmas successively (RF power: 200 W; pressure: 250 mT; flow rate gases: 6 sccm; plasma exposure time: 10 minutes).

EXAMPLES

The following materials and methodologies were utilized in the examples discussed further below.

High purity argon (Ar) and oxygen were purchased from Liquid Carbonic. 1,3 Propylenediamine (99+%) (PD), hexafluoro 1,3 propylenediamine (HFPD), hexafluoroglutaric anhydride (97%) (HFGA), pentafluoropropionic anhydride (99+%) (PFPA), and pentafluorophenyl bezaldehyde (PFB) were supplied by Aldrich Co.

The reagents, the technique used for immobilizing the enzyme α-chymotrypsin (AC), and the assay for monitoring the enzyme activity are as described in R. Ganapathy, et al., J. Biomater. Sci. Polymer Edn., Vol. 9, No. 4, 1999, pp. 389–404. Immobilization of AC was carried out according to the following procedure: functionalized substrates were dipped into 25 ml of 0.02 M-(hydroxyethyl) piperazine-N'-(3-propane sulfonic acid) (EPPS) buffer solution. The pH of the solutions were corrected to 8.7 by adding 1 N NaOH, then 13 mg of AC was added to each solution and the solutions were kept for 45 minutes. 0.02 M sodium cyanoborohydride was then added and the substrates were suspended for 1 h. At the end of the procedure, the samples were washed with the buffer and then with distilled water. The samples with attached AC were also swelled in dimethyl sulfoxide (DMSO) and tetrachloroethylene (TCE) respectively and washed extensively with buffer and water in order to remove non-covalently-bonded AC. 1 mM solution of 1.2 ml acetyl tyrosine ethyl ester (ATEE) and 0.15 M of 8.8 ml NaCl containing 0.5% (v/v) of Triton X-100 was used for the assay to estimate the activity of the immobilized enzyme. The pH change of the solutions were monitored.

Dichlorosilane (DS) was supplied by Gelest Inc. (lecture bottle) and it was used as received. Aldrich, atactic polystyrene(APS) (Mw: 400,000) and isotactic polystyrene (IPS) (90%, Mw: 400,000) substrates (discs of 4 cm diameter and thickness of 1 mm) were prepared using hot pressing technique (temperature of the die: 100° C.; pressure: one ton/cm$^2$; vacuum environment, the discs were removed after cooling the die to room temperature). Additive-free polyethylene (PE) films (W. R. Grace & Co.) were used as received. APS, IPS and PE film samples were acetone extracted then washed with water and dried under vacuum oven conditions. Comparative survey and high resolution X-ray photoelectron spectroscopy for chemical analysis (ESCA) evaluations indicated that the samples do not contain detectable amounts of additives on their surfaces. Accordingly all plasma treatment processes were carried out on samples as received.

Derivatization resulting in the implantation of carbonyl groups was performed in liquid media as described in F. Denes, et al., J. Macromol. Sci. Pure and Appl. Chem., Vol. 32, Nos. 8 & 9, 1995, pp. 1405, et seq. The polymer samples (5 cm$^2$) were immersed for 2 hours at 25° C. in solutions containing 150 mg pentafluorophenyilhydrazin (PFPH) and 1 drop of concentrated HCL in 15 ml 95% ethanol. The substrates were then washed with 100% ethanol and extracted with ether. Primary amine functionalities were labeled by an in situ gas phase reaction using PFB. Over the freshly functionalized polymeric substrates, PFB was distilled and the samples were kept under 1000 mT vapor pressure for 20 minutes. Vacuum dried samples were used for ESCA evaluations.

Covalent attachments of spacer molecular chains were performed using a direct reaction, a one stage reaction, and a three stage reaction. Direct immobilization of AC was performed involving plasma generated C=O functionalities. During the one-stage reaction, HFGA vapors were introduced (in situ) over DS-plasma functionalized polymer surfaces under vacuum (vapor pressure of HFEGA: 1000 mT, reaction time: 20 minutes; after the reaction was completed, the reactor was vacuumed to basic-pressure level). The three-step process was completed by introducing, for instance, over DS-plasma functionalized polymer surfaces, HFGA, PD and HFGA consecutively. All sequences were performed at 1000 mT pressure, 20 minutes reaction time, and by creating base pressure conditions between the consecutive steps.

Evaluation of the relative surface atomic compositions of plasma modified, derivatized and enzyme attached samples were carried out using a Perkin Elmer Physical Electronics 0 5400 small area ESCA system; Mg source; 15 kV; 300 W; pass energy: 89.45 eV; angle: 45°. Carbon (C1s), oxygen (O1s), nitrogen (N1s), fluorine (F1s) atomic compositions were evaluated and the binding energy values of the non-equivalent positions of carbon linkages were analyzed. In order to correct surface-charge-origin binding energy shifts calibrations were performed based on the well known C1s peak.

Differential Attenuated Total Reflectance Fourier-Transform Infrared Spectroscopy (ATR-FTIR) was used to identify AC-related chemical linkages on plasma functionalized and enzyme-immobilized polymer surfaces. An ATI-Mattson, Research Series IR instrument was used which was provided with a GRASEBY-Special Benchmark Series ATR in-compartment P/N/11160 unit. All FTIR evaluations were performed under a nitrogen blanket generated from a flow-controlled liquid nitrogen tank. Data were collected in the 600–4000 cm$^{-1}$ wavenumber region with 250 scans for each sample, with a resolution of 0.4 cm$^{-1}$. The differential spectra resulted from the subtraction of reference spectra (ATR spectra of surface-functionalized polymers) from the immobilized enzyme-coated polymer ATR spectra were also recorded.

The presence of covalently attached AC on PE substrates was also monitored using laser desorption Fourier transform ion cyclotron resonance mass spectrometry (LD-FT/ICR/MS). A Finnigan FT/MS Newstar system (Madison, Wis.) operating at 3.0 tesla with the standard dual-trap configuration was used in all studies. Experimental control and data interpretation were accomplished by use of Odyssey software running on Sun Microsystem (Mountain View, Calif.) computer station. The modified samples placed on the sample-holder discs were positioned, with the aid of an automatic insertion probe, approximately 3 mm away from the source trap plate of the ICR cell. The source pressure was less than 3.0×10$^{-7}$ torr (uncorrected ion gauge reading) for all mass evaluations. A Tachisto $CO_2$ (Needham, Mass.) laser beam ($\lambda$=10.6 μm, power 10$^6$–10$^8$ watts/cm$^2$, pulse width =40–80 ns) was fired at the sample-disc producing a spot size of approximately 1 mm$^2$. The desorbed neutral materials were allowed to drift into the cell for 4 msec. and subsequently ionized with a 70 eV electron beam. The source trap plate was set 2.0 V and the back trap plate (conductance limit) was held at 2.0 V (64 K data points). After 2.0 second delay ions were excited by use of linear sweep excitation prior to detection. One zero fill was performed prior to Fourier transformation.

Plasma induced modifications of surface morphologies of polymer substrates and the new topographies generated as a result of enzyme attachments were evidenced by atomic force microscopy (Digital Instrument Nanoscope III AFM; experimental conditions: scan rate: 2.654 Hz; sampling number: 512).

Conformational modeling of spacer molecules (optimizing models, conformational searching and calculating single point energies for molecules) was performed using computational tools provided by Chem3D Pro (Version 4, CambridgeSoft, Cambridge, Mass., USA), based on molecular mechanics. Global minimum-conformations, as well as all-conformations that contribute significantly to the experimental properties, were computed using Conformer (Princeton Simulations, New Brunswick, N.J., USA). Conformer directly uses the Chem3D-MM2 force field.

The reproducibility of plasma-induced modifications and enzyme immobilization reactions were tested by running ten different plasma and immobilization procedures, under similar experimental conditions. Enzyme-activity assay tests were run for 5 and 20 minute intervals, and the enzyme activity was also tested by re-using thoroughly-washed, enzyme-immobilized substrates for as many as 5 cycles.

DS-plasma functionalization reactions were carried out in a capacitively coupled, parallel-plate (disc-shaped electrodes, diameter: 20 cm, gap between the electrodes: 3 cm); cylindrical, stainless steel reactor of the type 20 equipped with 40 kHz and 13.46 MHz RF power supplies (40 kHz: PE 1000 PT AC Plasma Source, 1000 W; 13.56 MHz: RF-Power Products Inc., 1000 W, Model 7522328010). In a typical experiment, after the specific polymeric substrate was introduced into the reactor, and base pressure was created in the system, then DS vapors were introduced, at the selected pressure and flow-rate condition, into the reactor. The plasma was ignited in the following step, and the discharge was sustained for the pre-selected reaction-time. At the end of the plasma-reaction the reactor was evacuated to base-pressure level, followed by in situ second stage functionalization processes in the absence of plasma. During the plasma exposures the following experimental conditions were used: lower electrode: grounded; upper electrode: connected to the 40 kHz RF-power-supply; base pressure: 40 mT; pressure in the absence of plasma: 200 mT; pressure in the presence of plasma: 220 mT; RF-power: 100 W; treatment time: 30 seconds; flow rate DS: 6 sccm.

For convenience, the following summarizes the abbreviations/acronyms for the materials used in these examples:

PD=1,3 propylenediamine
HFPD=hexafluoro 1,3 propylenediamine
HFGA=hexafluoroglutaric anhydride
PFPA pentafluoropropionic anhydride
PFB=pentafluorophenyl bezaldehyde
AC=α-chymotrypsin
DS=dichlorosilane
APS=atactic polystyrene
IPS=isotactic polystyrene
PE=polyethylene
PFPH=pentafluorophenylhydrazin
EPPS=N-(hydroxyethyl) piperazine-N'-(3-propane sulfonic acid)
DMSO=dimethyl sulfoxide
TCE=tetrachloroethylene
ATEE=acetyl tyrosine ethyl ester PE is an inexpensive, fairly thermally stable, lightweight (density: 0.9–0.92 g/cm$^3$) polymer. However, due to its high crystallinity and the absence of reactive functionalities, it is chemically inert, which excludes most of the conventional wet-chemistry techniques for potential functionalization processes. Due to the comparable energy levels of cold-plasma species (electrons, ions of either polarity, free radicals, excited species, etc.) with the bond energies of most of the chemical compounds in accordance with the invention, glow discharge environments can be used to functionalize even the most inert polymeric structures under mild temperature conditions (close to room temperature).

Figure 4:
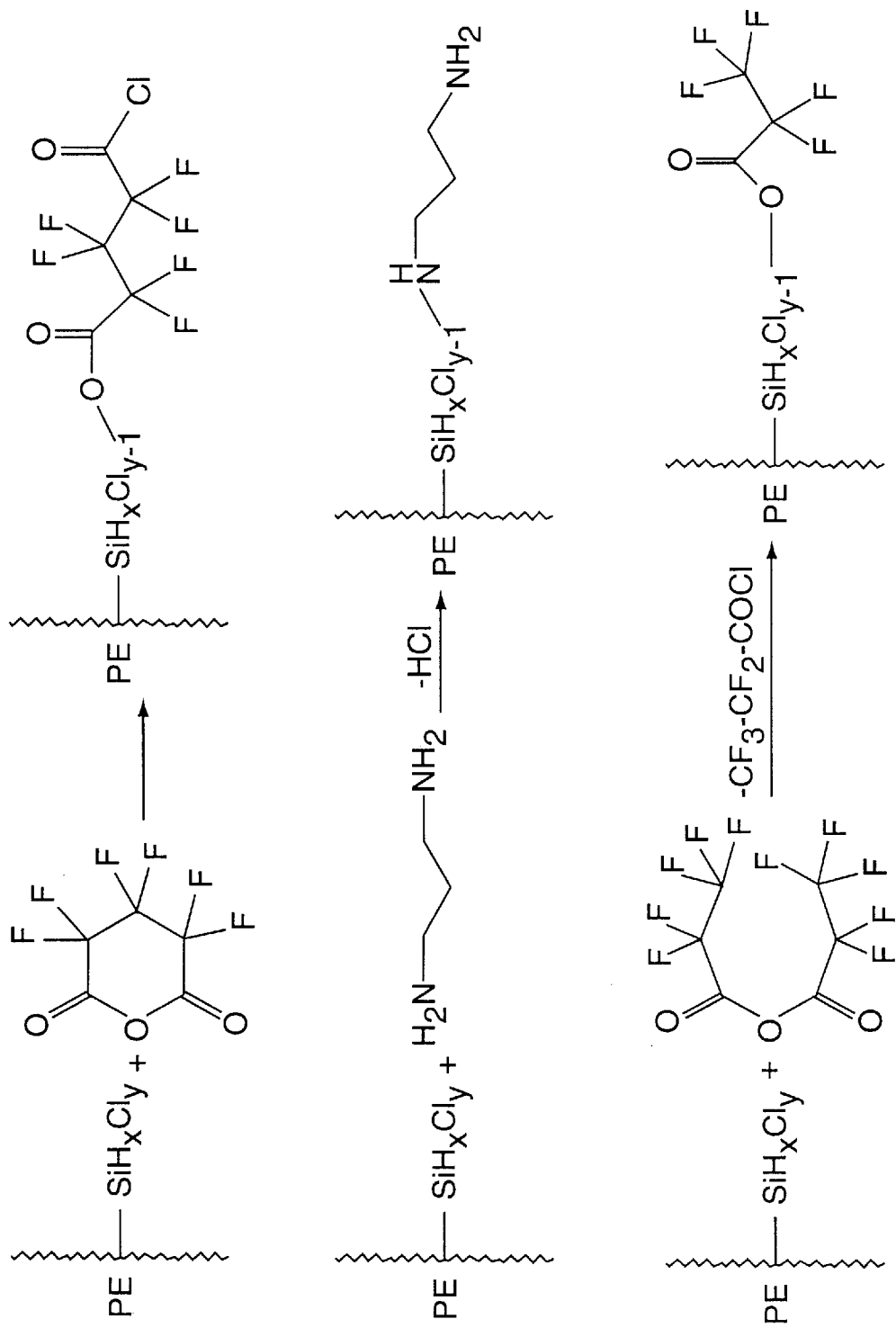
FIG. 4 are chemical diagrams illustrating reaction schemes for covalently anchoring spacer molecules to a functionalized substrate to expose the required functional groups at the free ends of the spacer molecules.

Plasma-generated silicon-hydrogen-chlorine ($SiH_xCl_y$—) functionalities were implanted onto PE film surfaces and used in a subsequent step, under in situ (vacuum) conditions, for covalently anchoring spacer molecules, which expose the required functional groups at their free ends, in accordance with the reaction scheme illustrated in FIG. 4.

Figure 5:
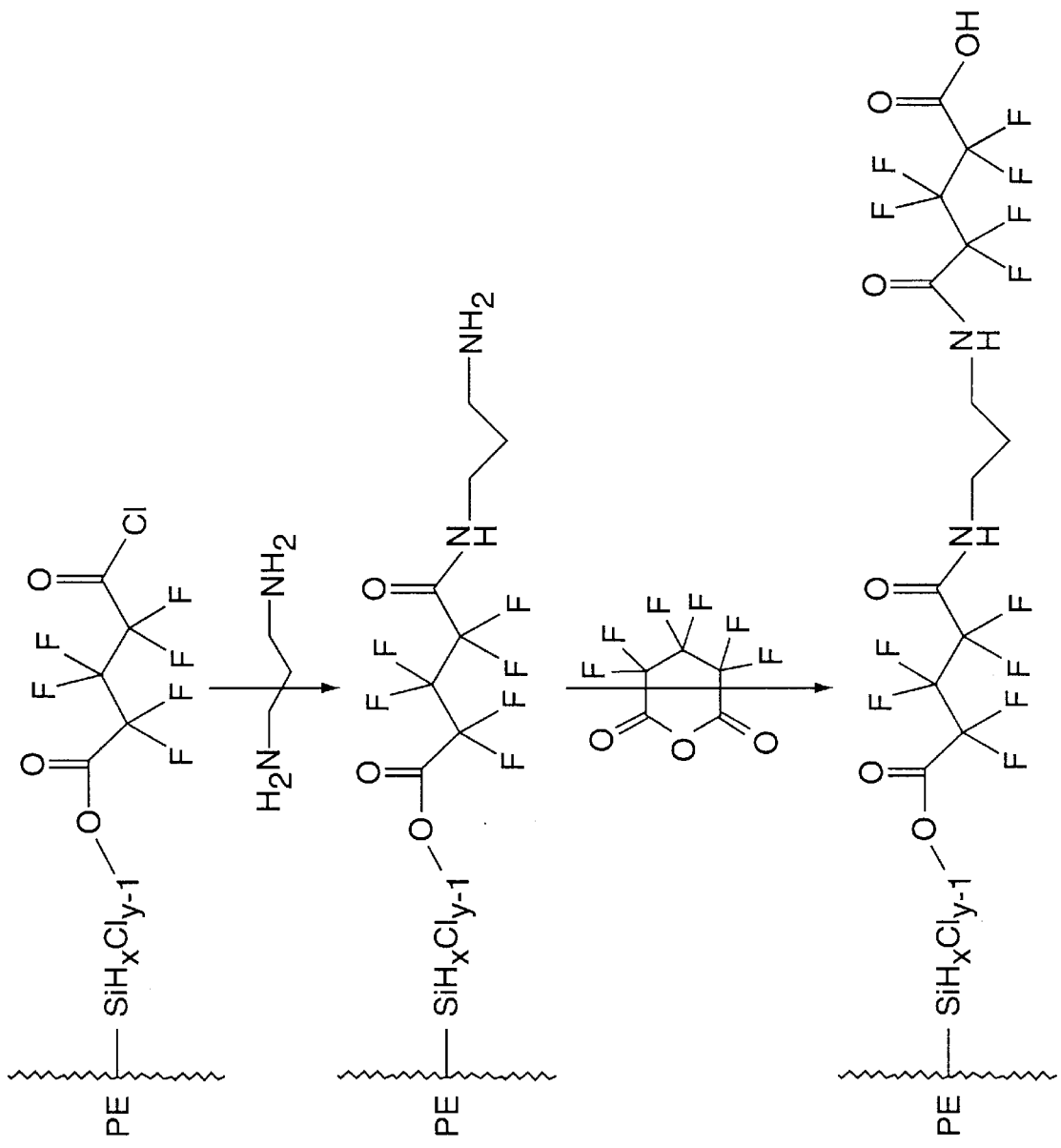
FIG. 5 are chemical diagrams illustrating the reaction scheme for covalently linking α-chymotrypsin to spacer molecules through various combinations of reactants to provide molecular chains between the enzyme and the substrate.

These functional groups are then capable of covalently-linking AC through a spacer, that is, molecular chains based on various combinations of DS, HFGA, PD, HFPD, PFPA, and HFGA-PD-HFGA molecular chains between the AC and the PE substrate, in accordance with the reaction scheme illustrated in FIG. 5.

Figure 6:
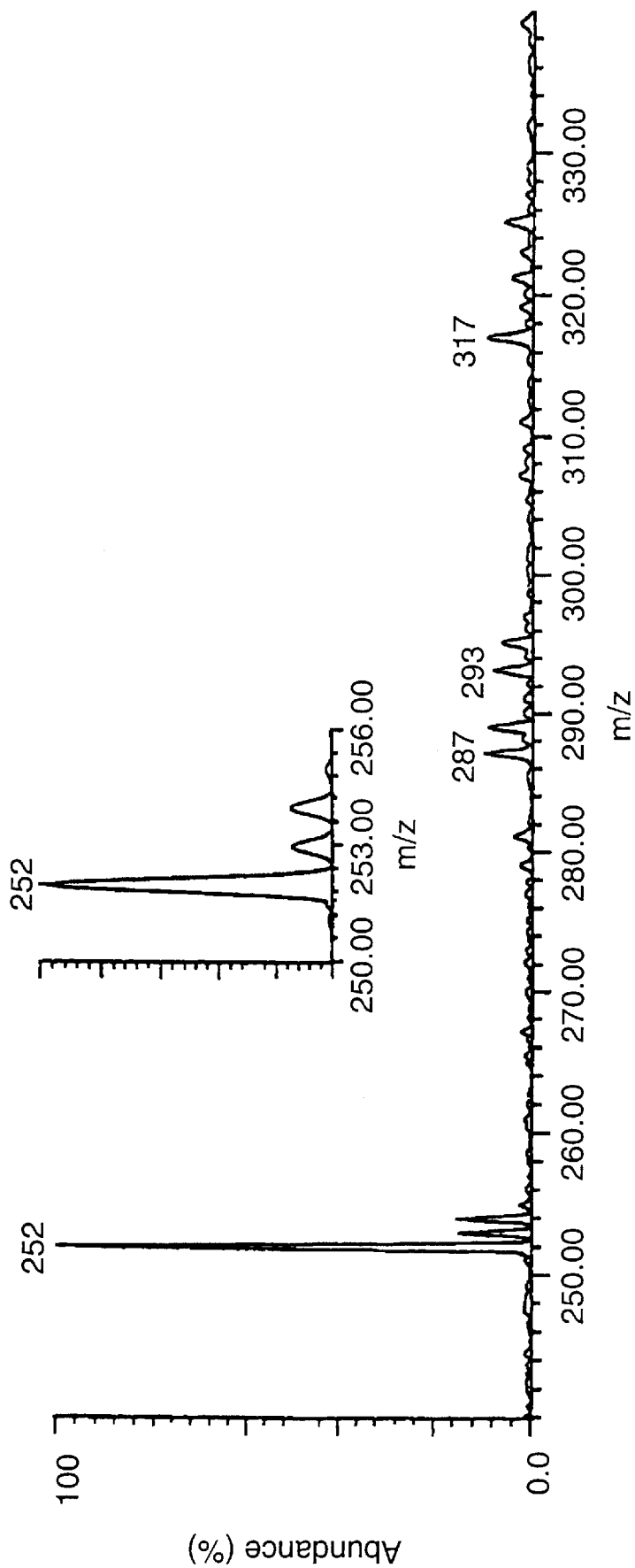
FIG. 6 are mass spectrometry spectra collected from free standing α-chymotrypsin.
Figure 7:
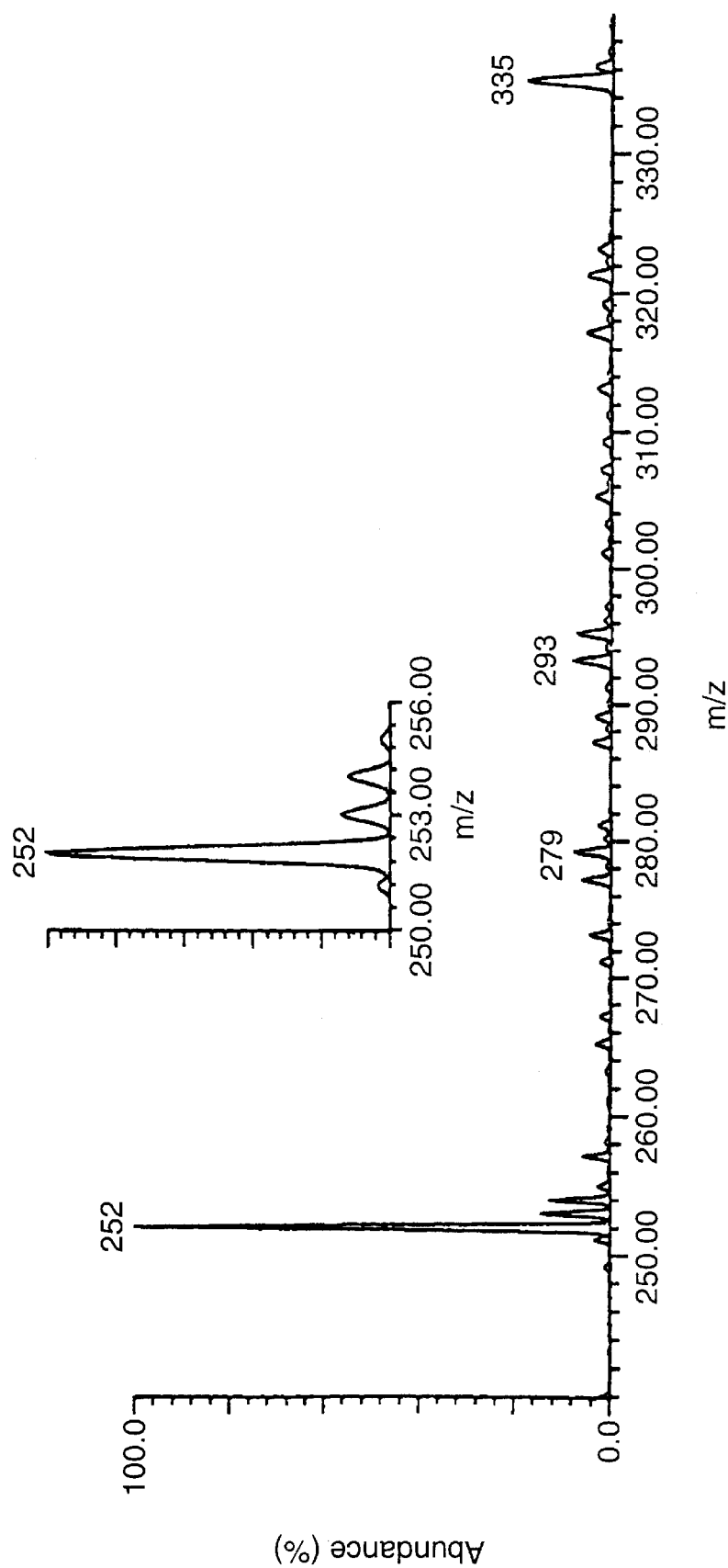
FIG. 7 are mass spectrometry spectral collected from α-chymotrypsin immobilized on a polyethylene substrate.

The presence of covalently-linked AC on PE substrate surfaces was demonstrated by comparative LD-FT/ICR/MS and differential ATR-FTIR spectroscopy. MS spectra collected from AC and intensely washed AC-immobilized PE shown in FIGS. 6 and 7, respectively, exhibit almost identical fragmentation patterns in the 250–255 m/z region, while these peaks are totally absent in the spectrum of virgin PE.

Figure 8:
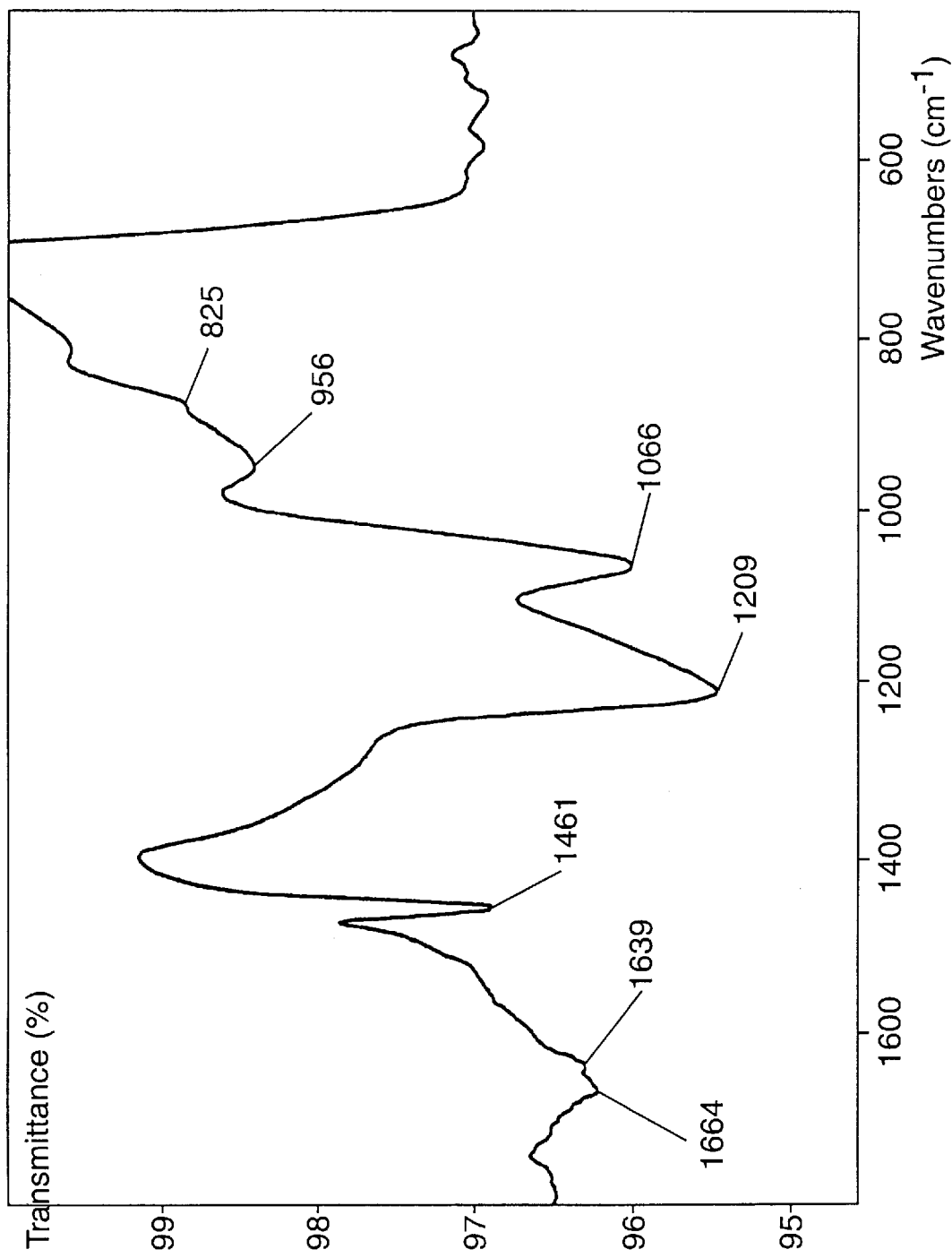
FIG. 8 is a graph of differential ATR-FTIR data collected from DS-HFGA-spacer-mediated-α-chymotrypsin immobilized on polyethylene.
Figure 9:
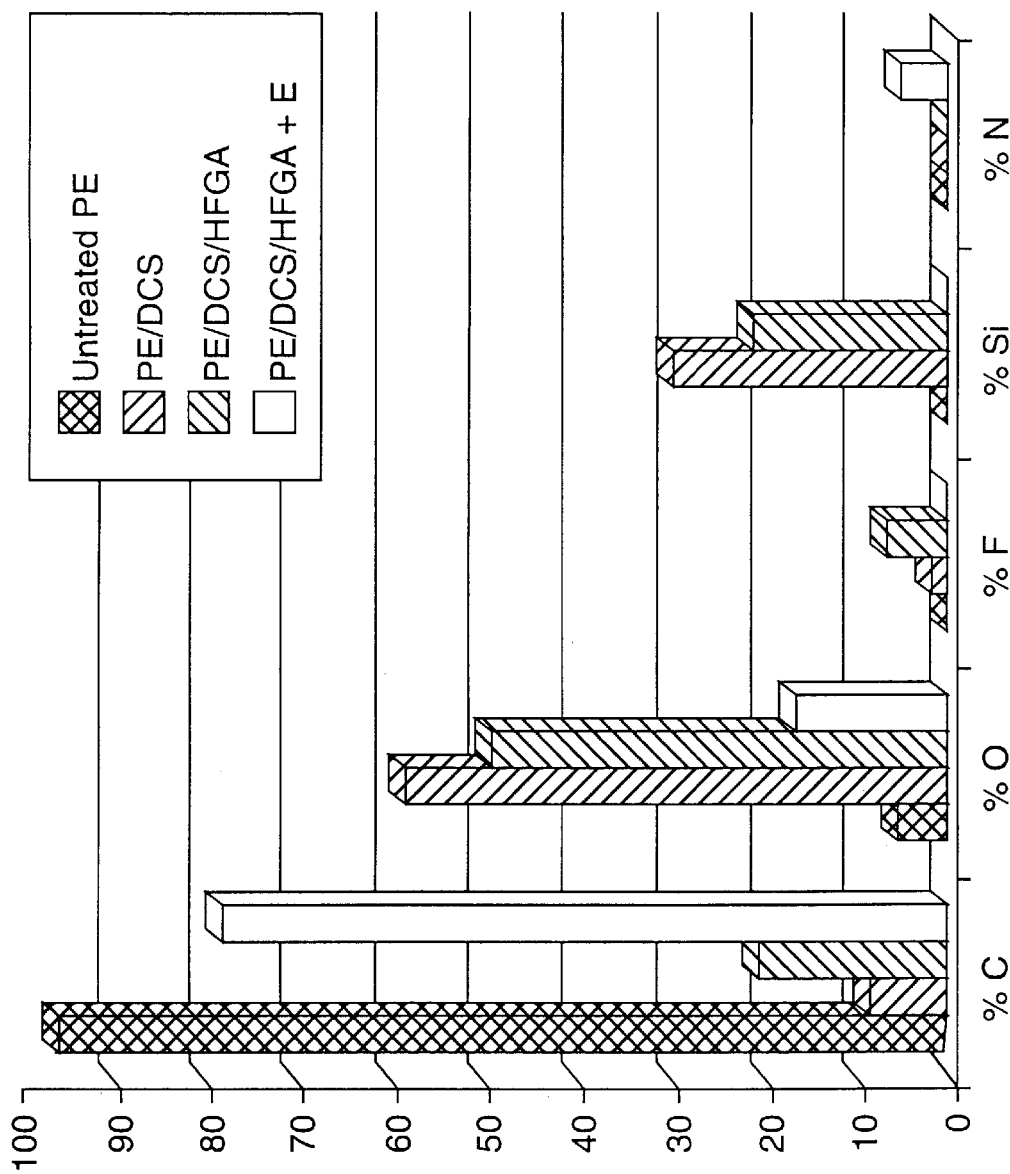
FIG. 9 are bar graphs illustrating survey ESCA origin relative surface atomic compositions of untreated polyethylene, DS functionalized polyethylene, DS-HFGA functionalized on the polyethylene, and DS-HFGA functionalized and α-chymotrypsin immobilized therewith on a polyethylene substrate.

Differential ATR-FTIR data collected from virgin and DS-HFGA-spacer-mediated-AC-immobilized PE shown in FIG. 8 confirm the presence of covalently attached enzyme on the functionalized PE surfaces. Comparing the two specific absorption regions, at 1500–1750 cm$^{-1}$ (which is the vibration-region characteristic for peptide linkages) and 1000–1250 cm$^{-1}$ (vibration-zone peculiar for Si—O—Si, C—O—Si and $CF_2$ functionalities), one can observe that these specific wavenumber ranges are fairly intense in the differential spectra, while they are totally absent in the spectra of virgin PE. The absorptions at 1664 and 1639 cm$^{-1}$ wavenumbers were assigned to C=O absorption from secondary amides and amide I band from secondary amides. The 1066 cm$^{-1}$ and 1209 cm$^{-1}$ vibrations are characteristic for Si—O—Si—, Si—O—C, and CF from $CF_2$ groups. The narrow 1461 cm$^{-1}$ vibration peculiar for PE ($CH_2$ bending) is still visible after the subtraction of the spectra.

Figure 10:
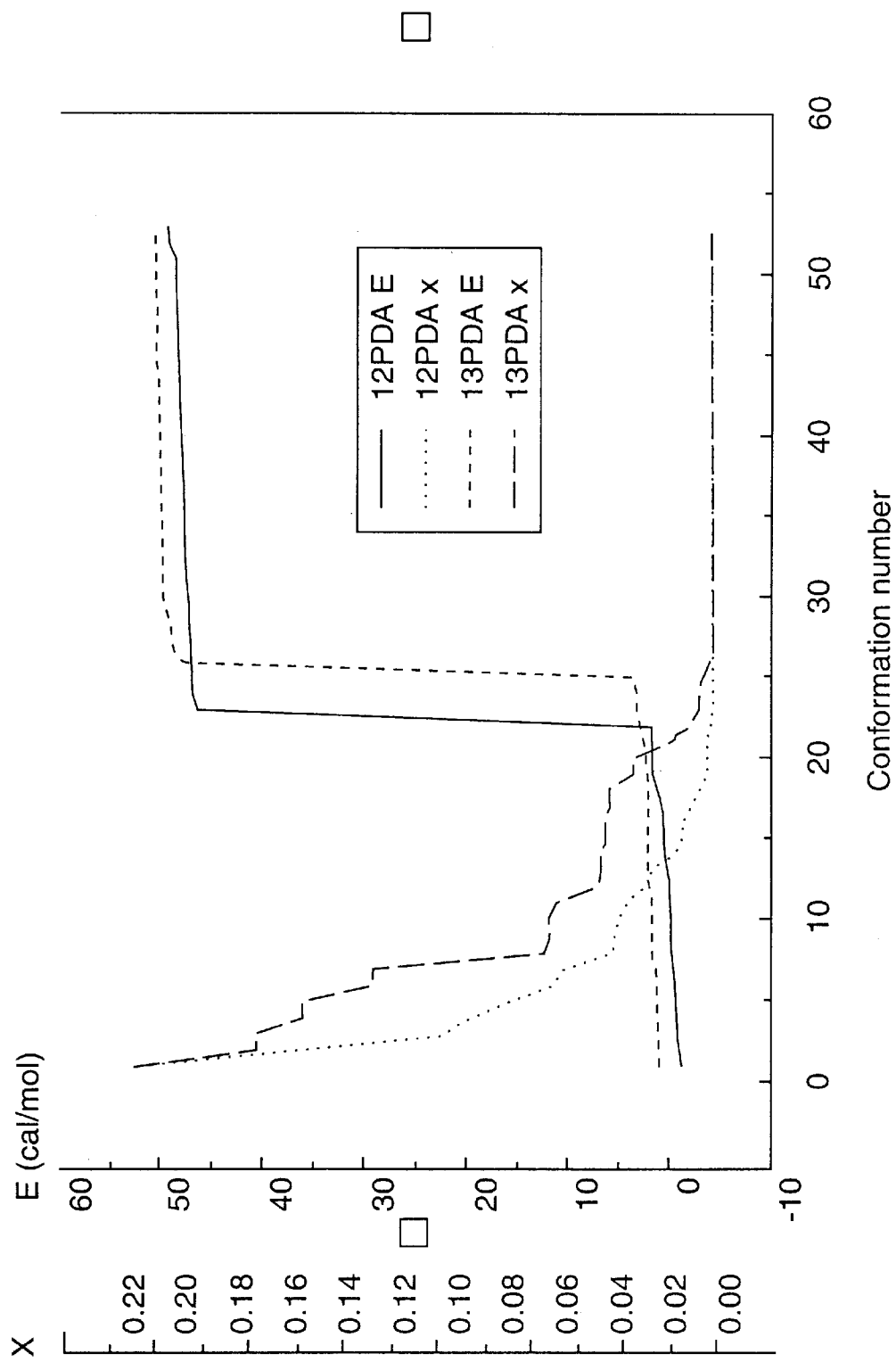
FIG. 10 is a plot of energy (E) and probability (X) for different conformations of 1, 2 TD and 1,3 TD.

Survey ESCA-origin relative surface atomic compositions of untreated PE, DS, DS-HFGA functionalized PE, and DS-HFGA functionalized and AC-immobilized PE shown in FIG. 10 (OS is referred to as DCS in this figure), reflect the atomic concentration changes according to the functionalization and immobilization reactions. The relatively high nitrogen atomic concentration of the AC containing surface and the high silicon and fluorine concentrations of DS-HFGA functionalized substrates indicate the development of successful derivatization and immobilization reactions.

Linear spacer molecules dramatically change the morphologies of the anchored enzyme molecules. Atomic force microscope images reveal that the globular (clustered) topographies of directly connected AC (C=O groups mediated covalent coupling) is replaced by filigree (fiber-clusterlike) organizations. It was observed that fiber-like morphologies are initiated when spacer molecules are attached to the PE surface. It is suggested that the spacer-chain-mediated, enhanced molecular freedom of motion of the enzyme allows the packing of AC molecules into specific supramolecular structures.

The AC-assay test is based on the hydrolysis of the ester bond of acetyl tyrosine ethyl ester (ATEE) which results in the formation of acetyl tyrosine acid. The pH of the medium will decrease with the reaction, which is the measure of the activity of the immobilized enzyme. Table 1 below indicates the pH values measured after 5 and 25 minutes contact of treated PE-substrates with the immobilized AC. Various substrates without linker molecules, and the free enzyme itself, were also tested for comparison purposes and the results are listed in Table 1.

TABLE 1 pH values measured after 5 and 25 minutes contact of the PE-substrate having the immobilized AC (pH of ATEE solution is 7.8 ± 0.1)

| No. | Substrate Used | pH after 5 Minutes | pH after 25 Minutes |
|---|---|---|---|
| 1 | Free Enzyme | 4.8 | 4.8 |
| 2 | PET and Oxygen Plasma | 7.1 | 6.6 |
| 3 | APS and Oxygen Plasma | 7.0 | 6.3 |
| 4 | IPS and Oxygen Plasma | 7.0 | 6.3 |
| 5 | PE and Oxygen Plasma | 7.0 | 6.0 |
| 6 | PE/DS/tetrafluoropropionic anhydride | 6.9 | 6.0 |
| 7 | PE/DS/HFGA | 5.8 | 5.3 |
| 8 | PE/DS/HFGA/PD/HFGA | 5.5 | 4.9 |
| 9 | PE/DS/HFGA/PD | 7.0 | 5.9 |
| 10 | Control experiment (without enzyme) | 7.8 | 7.8 |

Several observations can be made based on the data. First, C=O functionalized polymer surfaces allow efficient immobilization of AC regardless of the nature of the substrate, PET, PS or PE. However, the activities of the immobilized enzymes are significantly lower in comparison to the free enzyme. Second, the stereoregular nature of PS substrates does not influence the activity of immobilized AC. Third, HFGA- and HFGA-HFPD-HFGA-origin spacer molecules intercalated between the PE substrate and AC molecules distinctly improve the activity of AC. Fourth, DS-PD spacer-molecules do not influence dramatically the activity of AC. This might be explained by the low availability (possible conformational restrictions) of enzyme-side-chain functionalities capable of reacting with primary amine groups (e.g., COOH, or C=O groups).

It should be noted that all pH data represent average values from at least five different substrates, and that the activities of immobilized systems were almost identical in ten consecutive cycles, by reusing thoroughly washed identical substrates. The only exception was the HFGA-PD-HFGA spacer linked AC, which had the best activity, but the enzyme lost some of its activity (9.5%) in consecutive washing/assay cycles. This might be related to the low pH values generated during the assay which can be responsible for the deactivation of the AC.

Conformational modeling of 1, 2 and 1,3 PD indicates that the most probable conformation of 1, 2 PD is where the distance between the primary amine groups is 2.86 Å. This would most likely lead to the double attachment of this spacer to a functionalized surface or would make the amine groups less available for further anchoring mechanisms. For a conformation where the amine groups are more distant (4.81 Å) the probability of the existence of this structure is negligible. In the case of 1, 3 PD, the linear conformation (distance between the primary amine groups: 4.95 Å) is significantly higher (8.9–9.8%) relative to the bent structure (distance between the primary amine groups: 2.87 Å, which is comparable to both 1,2 PD distances).

Conformational calculations performed on HFPD-HFGA and HGA-HFPD-HFGA spacer chains attached to $SiCl_2H_2$-plasma functionalized PE show that the longer the spacer chain, the higher the distance (12.9 Å) between the functional chain-ends of the most probable conformational structure and the substrate. This suggests that the activity of the immobilized AC is strongly dependent on the spacer-length-controlled freedom of movement and the availability of the active site of the enzyme, which is in good agreement with the experimental findings.

Conformational modeling of non-substrate attached HFGA-PD-HFGA chains shows that regardless of the higher or lower probabilities of conformations (e.g., 70.2, 17.5, 11.7 and 0.6%) the distance between the two polar end-groups of the chains are very similar. This suggests that besides the length of the spacer chains their chemical nature also will influence significantly the spacer mediated distance between the substrate and the anchored biomolecules.

Figure 11:
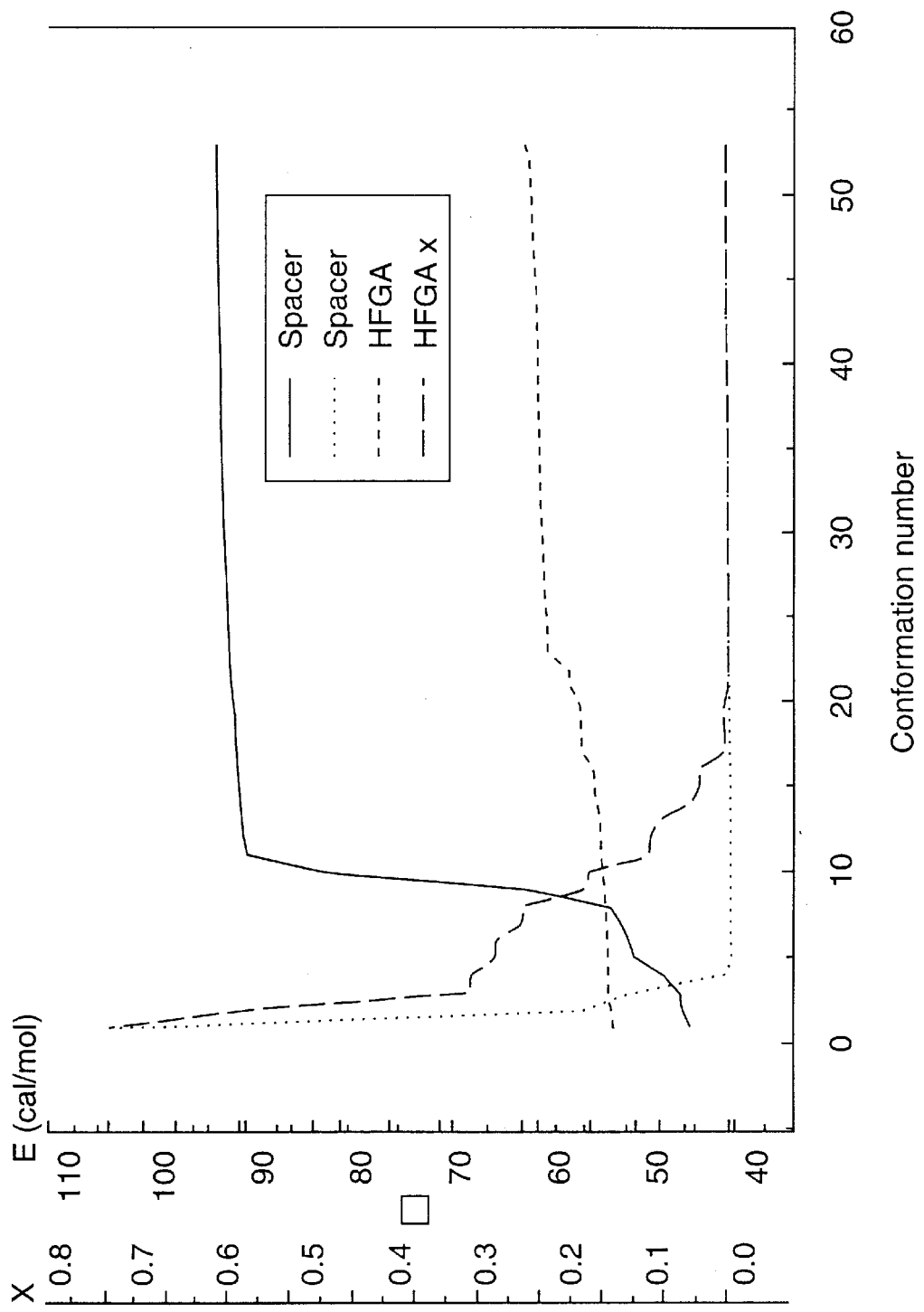
FIG. 11 is a plot of energy (E) and probability (X) for different conformations of HFGA and spacer molecules (HFGA/PD/HFGA).

The probability/number of conformation distribution diagrams shown in FIGS. 10 and 11 indicate that significant conformational probabilities are distributed on higher number of conformations in the case of 1,2 PD and HFGA-HFPD-HFGA systems. This indicates the presence of a more intense segmental mobility and consequently a more intense enzyme mobility.

The foregoing examples illustrate that the tacticity of the polystyrene substrates does not influence the activity of the immobilized enzyme. Further, the longer the enzyme-anchoring spacer chain, the higher the activity of the immobilized AC. Conformational modeling correlated with the length of spacer chains and enzyme activity indicates that the freedom of mobility of AC is strongly related to the activity and supramolecular order of the immobilized enzyme. The stability of the immobilized AC is remarkable; it retains its activity after several washing/assay cycles. Thus, the process of the invention enables many practical applications of the plasma-enhanced immobilization of enzymes.

Table 2 below summarizes various exemplary treatment conditions in accordance with the invention. These are provided as examples only, and it is understood that the invention is not limited to the substrates or the treatment parameters listed.

TABLE 2

| | Substrate | Reactor | Reactor Conditions |
|---|---|---|---|
| 1 | $SiH_xCl_y$-functionalities/primary amines | Glass | Parallel Plate | Dichlorosilane plasma 150–500 mTorr 40 KHz power supply 50–300 W |

TABLE 2-continued

| | | Substrate | Reactor | Reactor Conditions |
|---|---|---|---|---|
| 2 | SiH$_x$Cl$_y$-functionalities/primary amines | Silica Beads | Parallel Plate | 0.5–2 min. treatment time<br>Diamino reaction (1,2-diamino ethane; 1,2-diamino propane; 1,3-diamino propane, etc.) - Spacer<br>1–10 Torr<br>0.5–2 hours<br>Dichlorosilane plasma<br>150–500 mTorr<br>40 KHz power supply<br>50–300 W<br>0.5–2 min. treatment time<br>Diamino reaction (1,2-diamino ethane; 1,2-diamino propane; 1,3-diamino propane, etc.) - Spacer<br>1–10 Torr<br>0.5–2 hours |
| 3 | SiH$_x$Cl$_y$-functionalities/primary amines | Silica Beads | External electrodes/Rotating reactor | Dichlorosilane plasma<br>150–500 mTorr<br>13.56 MHz power supply<br>50–300 W<br>0.5–2 min. treatment time<br>Diamino reaction (1,2-diamino ethane; 1,2-diamino propane; 1,3-diamino propane, etc.) - Spacer<br>1–10 Torr<br>0.5–2 hours |
| 4 | SiH$_x$Cl$_y$-functionalities/primary amines | Polycarbonate | Parallel plate | Dichlorosilane plasma<br>150–500 mTorr<br>40 KHz power supply<br>50–300 W<br>0.5–2 min. treatment time<br>Diamino reaction (1,2-diamino ethane; 1,2-diamino propane; 1,3-diamino propane, etc.) - Spacer<br>1–10 Torr<br>0.5–2 hours |
| 5 | SiH$_x$Cl$_y$-functionalities/primary amines | Polycarbonate | Parallel Plate | Dichlorosilane plasma<br>150–500 mTorr<br>13.56 MHz power supply<br>50–300 W<br>100–900 µs pulsing period<br>20–80% duty cycle<br>1–30 min. treatment time<br>Diamino reaction (1,2-diamino ethane; 1,2-diamino propane; 1,3-diamino propane, etc.) - Spacer<br>1–10 Torr<br>0.5–2 hours |
| 6 | SiH$_x$Cl$_y$-functionalities/primary amines | Polyethylene (film) | Parallel Plate | Dichlorosilane plasma<br>150–500 mTorr<br>40 KHz power supply<br>50–300 W<br>0.5–2 min. treatment time<br>Diamino reaction (1,2-diamino ethane; 1,2-diamino propane; 1,3-diamino propane, etc.) - Spacer<br>1–10 Torr<br>0.5–2 hours |
| 7 | SiH$_x$Cl$_y$-functionalities/primary amines | Polyethylene (film) | Parallel Plate | Dichlorosilane plasma<br>150–500 mTorr<br>13.56 MHz power supply<br>50–300 W<br>100–900 µs pulsing period<br>20–80% duty cycle<br>1–30 min. treatment time<br>Diamino reaction (1,2-diamino ethane; 1,2-diamino propane; 1,3-diamino propane, etc.) - Spacer<br>1–10 Torr<br>0.5–2 hours |
| 8 | SiH$_x$Cl$_y$-functionalities/primary amines | Polyethylene (powder) | Parallel Plate | Dichlorosilane plasma<br>150–500 mTorr<br>13.56 MHz power supply<br>50–300 W<br>0.5–2 min. treatment time<br>Diamino reaction (1,2-diamino ethane; 1,2-diamino propane; 1,3- |

TABLE 2-continued

| | Substrate | Reactor | Reactor Conditions |
|---|---|---|---|
| | | | diamino propane, etc.) - Spacer |
| | | | 50–300 Torr |
| | | | 0.5–2 hours |
| 9 | SiH$_x$Cl$_y$- functionalities/ primary amines | Silica beads | Parallel Plate | Dichlorosilane plasma |
| | | | 150–500 mTorr |
| | | | 40 KHz power supply |
| | | | 50–300 W |
| | | | 0.5–2 min. treatment time |
| | | | Diamino reaction (1,2-diamino ethane; 1,2-diamino propane; 1,3-diamino propane, etc.) - Spacer |
| | | | 1–10 Torr |
| | | | 0.5–2 hours |
| | | | Diamino reaction (oxalyl chloride; hexafluoroglutaric anhydride; hexafluoroglutaryl chloride etc.)-Spacer |
| | | | 1–10 Torr |
| | | | 0.5–2 hours |
| 10 | SiH$_x$Cl$_y$- functionalties/ primary amines Long spacer | Silica beads | Parallel Plate | Dichlorosilane plasma |
| | | | 150–500 mTorr |
| | | | 40 KHz power supply |
| | | | 50–300 W |
| | | | 0.5–2 min. treatment time |
| | | | Diamino reaction (1,2-diamino ethane; 1,2-diamino propane; 1,3-diamino propane, etc.) - Spacer |
| | | | 1–10 Torr |
| | | | 0.5–2 hours |
| | | | Diamino reaction (oxalyl chloride; hexafluoroglutaric anhydride; hexafluoroglutaryl chloride etc.)-Spacer |
| | | | 1–10 Torr |
| | | | 0.5–2 hours |
| | | | Diamino reaction (1,2-diamino ethane; 1,2-diamino propane; 1,3-diamino propane, etc.) - Spacer |
| | | | 1–10 Torr |
| | | | 0.5–2 hours |
| | | | Diamino reaction (oxalyl chloride; hexafluoroglutaric anhydride; hexafluoroglutaryl chloride etc.)-Spacer |
| | | | 1–10 Torr |
| | | | 0.5–2 hours |

It is understood that the invention is not limited to the embodiments set forth herein for illustration, but embraces all such forms thereof as come within the scope of the following claims.

What is claimed is:

1. A method of treating a surface of a substrate to functionalize the surface comprising:
   (a) igniting a cold plasma in a reactor reaction chamber in a gas selected from the group consisting of dichlorosilane, silicon tetrachloride, hexachlorodisilane, and mixtures thereof;
   (b) exposing the substrate surface to the plasma for a selected period of time sufficient to react the plasma with the substrate to implant silicon-chlorine functionalities into the substrate surface;
   (c) terminating the plasma and evacuating the gas from the reaction chamber; and
   (d) introducing into the evacuated reaction chamber a reactant gas which will bind with the silicon-chlorine functionalities for a selected period of time to provide covalent bonding of the reactant gas molecules with the silicon-chlorine functionalities to provide linked spacer molecules attached to the substrate.

2. The method of claim 1 wherein igniting the cold plasma in the gas is carried out by capacitively coupling RF power to the gas.

3. The method of claim 1 wherein the substrate to be treated is selected from the group consisting of polymers and glasses.

4. The method of claim 1 wherein the reactant gas is selected from the group consisting of dichlorosilane (DS), hexafluoroglutaric anhydride (HFGA), 1, 3 propylenediamine (PD), hexafluoro 1, 3 propylenediamine (HFPD), and pentafluoropropionic anhydride (PFPA).

5. The method of claim 1 including the further step of exposing the treated substrate to biomolecules to bind the biomolecules to the spacer molecules.

6. The method of claim 1 including the further step of exposing the treated substrate to a solution containing an enzyme to bind the enzyme with the spacer molecules.

7. The method of claim 6 wherein the enzyme is α-chymotrypsin.

8. The method of claim 1 wherein the reactant gas is a first reactant gas, and including the further steps of evacuating the reaction chamber to remove the first reactant gas and introducing a selected second reactant gas which will bind with the molecules of the first reactant gas to form a chain of spacer molecules.

9. The method of claim 8 wherein the selected first and second reactant gases are hexafluoroglutaric anhydride (HFGA) and 1, 3 propylenediamine (PD) and the steps are performed to provide a chain of spacer molecules comprising at least hexafluoroglutaric anhydride (HFGA), 1, 3 propylenediamine (PD) and hexafluoroglutaric anhydride (HFGA) consecutively.

10. The method of claim 8 including the further step of exposing the treated substrate to a solution containing an enzyme to bind the enzyme to the spacer molecules.

11. The method of claim 10 wherein the enzyme is α-chymotrypsin.

12. The method of claim 8 wherein the substrate is formed of a material selected from the group consisting of polyethylene, polystyrene, polycarbonate and silica.

13. The method of claim 8 wherein the first and second reactant gases are selected from the group consisting of hexafluoroglutaric anhydride (HFGA), 1, 3 propylenediamine (PD), hexafluoro 1, 3 propylenediamine (HFPD), and pentafluoropropionic anhydride (PFPA).

14. A method of immobilizing a biomolecule on a surface of a substrate comprising:
    (a) exposing the surface of a substrate to a cold plasma ignited in gas in a reaction chamber for a selected period of time sufficient to react the plasma with the substrate to implant silicon-chlorine functionalities into the substrate surface, the gas selected form the group consisting of dichlorosilane, silicon tetrachloride, hexachlorodisilane, and mixtures thereof;
    (b) terminating the plasma and evacuating the gas from the reaction chamber;
    (c) introducing into the evacuated reaction chamber a reactant gas from a source which will bind with the silicon-chlorine functionalities, to provide bonding of the source gas molecules with the silicon-chlorine functionalities to provide linked spacer molecules attached to the substrate; and
    (d) exposing the treated substrate to biomolecules to bind the biomolecules with the linker molecules.

15. The method of claim 14 wherein the substrate to be treated is selected from the group consisting of polymers and glasses.

16. The method of claim 14 wherein the reactant gas is selected from the group consisting of dichlorosilane (DS), hexafluoroglutaric anhydride (HFGA), 1, 3 propylenediamine (PD), hexafluoro 1, 3 propylenediamine (HFPD), and pentafluoropropionic anhydride (PFPA).

17. The method of claim 14 wherein the biomolecule is an enzyme.

18. The method of claim 17 wherein the enzyme is α-chymotrypsin.

19. The method of claim 14 wherein the reactant gas is a first reactant gas, and including the further steps of evacuating the reaction chamber and exposing the substrate surface to a selected second reactant gas to form a chain of spacer molecules before the step of exposing the treated substrate to biomolecules.

20. The method of claim 19 wherein the selected first and second reactant gases are hexafluoroglutaric anhydride (HFGA) and 1, 3 propylenediamine (PD) and the steps are performed to provide a chain of spacer molecules comprising at least hexafluoroglutaric anhydride (HFGA), 1, 3 propylenediamine (PD) and hexafluoroglutaric anhydride (HFGA) consecutively.

21. The method of claim 19 wherein the substrate is formed of a material selected from the group consisting of polyethylene, polystyrene, polycarbonate and silica.

22. The method of claim 19 wherein the first and second reactant gases are selected from the group consisting of hexafluoroglutaric anhydride (HFGA), 1, 3 propylenediamine (PD), hexafluoro 1, 3 propylenediamine (HFPD) and pentafluoropropionic anhydride (PFPA).

23. A method of treating a surface of a substrate to functionalize the surface comprising:
    (a) enclosing the substrate in a reaction chamber;
    (b) evacuating the reaction chamber to a base pressure level;
    (c) supplying dichlorosilane gas to and establishing a selected dichlorosilane gas pressure in the reaction chamber;
    (d) igniting a cold plasma in the gas in the chamber and exposing the substrate surface to the plasma for a selected period of time sufficient to react the dichlorosilane plasma with the substrate to implant silicon-hydrogen-chlorine functionalities into the substrate surface; and
    (e) evacuating the reaction chamber to a base pressure level, establishing a selected pressure of a reactant gas within the reaction chamber from a source which will bind with the silicon-hydrogen-chlorine functionalities, and exposing the substrate surface to the gas for a selected period of time to provide covalent bonding of the reactant gas molecules with the silicon-hydrogen-chlorine functionalities to provide linked spacer molecules attached to the substrate.

24. The method of claim 23 wherein igniting the cold plasma in the gas in the chamber is carried out by capacitively coupling RF power to the gas in the chamber.

25. The method of claim 24 including providing capacitive electrodes in the reaction chamber and mounting the substrate with the surface to be exposed to the plasma between the capacitive electrodes, and wherein igniting the plasma in the gas in the chamber is carried out by applying RF power to the electrodes to capacitively couple RF power to the gas between the electrodes.

26. The method of claim 23 wherein the substrate to be treated is selected from the group consisting of polymers and glasses.

27. The method of claim 23 wherein the reactant gas is selected from the group consisting of dichlorosilane (DS), hexafluoroglutaric anhydride (HFGA), 1, 3 propylenediamine (PD), hexafluoro 1, 3 propylenediamine (HFPD), and pentafluoropropionic anhydride (PFPA).

28. The method of claim 23 including the further steps of removing the treated substrate from the reaction chamber and exposing the treated substrate to biomolecules to bond the biomolecules to the spacer molecules.

29. The method of claim 23 including the further steps of removing the treated substrate from the reaction chamber and exposing the treated substrate to a solution containing an enzyme to bind the enzyme with the spacer molecules.

30. The method of claim 29 wherein the enzyme is α-chymotrypsin.

31. The method of claim 27 wherein the reactant gas is a first reactant gas and including the further steps of evacuating the reaction chamber to a base pressure level and establishing a selected pressure of a second reactant gas within the reaction chamber and exposing the substrate to the second reactant gas to form a chain of spacer molecules.

32. The method of claim 31 wherein the selected first and second reactant gases are hexafluoroglutaric anhydride (HFGA) and 1, 3 propylenediamine (PD) and the steps are performed to provide a chain of spacer molecules comprising at least hexafluoroglutaric anhydride (HFGA), 1,3 propylenediamine (PD), and hexafluoroglutaric anhydride (HFGA) consecutively.

33. The method of claim 31 including the further step of removing the treated substrate from the reaction chamber and exposing the treated substrate to a solution containing an enzyme to bind the enzyme to the spacer molecules.

34. The method of claim 33 wherein the enzyme is α-chymotrypsin.

35. The method of claim 31 wherein the substrate is formed of a material selected from the group consisting of polyethylene, polystyrene, polycarbonate and silica.

36. The method of claim 31 wherein the first and second reactant gases are selected from the group consisting of hexafluoroglutaric anhydride (HFGA), 1, 3 propylenediamine (PD), hexafluoro 1, 3 propylenediamine (HFPD) and pentafluoropropionic anhydride (PFPA).

* * * * *

UNITED STATES PATENT AND TRADEMARK OFFICE
CERTIFICATE OF CORRECTION

PATENT NO. : 6,402,899 B1
DATED : June 11, 2002
INVENTOR(S) : Denes et al.

It is certified that error appears in the above-identified patent and that said Letters Patent is hereby corrected as shown below:

Column 5,
Line 5, please delete "i$_2$Cl$_x$" and replace it with -- Si$_2$Cl$_x$ --.
Line 64, delete "SiCl$_x$" and replace it with -- SiCl$_4$ --.

Column 10,
Line 9, delete "HFEGA:" and replace it with -- HFGA --.

Signed and Sealed this

Fifteenth Day of October, 2002

Attest:

Attesting Officer

JAMES E. ROGAN
*Director of the United States Patent and Trademark Office*